US006635875B1

(12) United States Patent
Bley et al.

(10) Patent No.: US 6,635,875 B1
(45) Date of Patent: Oct. 21, 2003

(54) INFRARED GAS ANALYZER AND METHOD FOR OPERATING SAID ANALYZER

(75) Inventors: Werner Grosse Bley, Bonn (DE); Günter Voss, Much (DE); Ulrich Döbler, Wermelskirchen (DE); Thomas Böhm, Köln (DE)

(73) Assignee: Inficon GmbH (DE)

( * ) Notice: Subject to any disclaimer, the term of this patent is extended or adjusted under 35 U.S.C. 154(b) by 0 days.

(21) Appl. No.: 09/890,979

(22) PCT Filed: Jan. 20, 2000

(86) PCT No.: PCT/EP00/00407

§ 371 (c)(1),
(2), (4) Date: Aug. 6, 2001

(87) PCT Pub. No.: WO00/55603

PCT Pub. Date: Sep. 21, 2000

(65) Prior Publication Data (65)

(30) Foreign Application Priority Data

Mar. 13, 1999 (DE) .......................................... 199 11 260

(51) Int. Cl.$^7$ ................................................. G01N 21/61
(52) U.S. Cl. ....................................... 250/345; 250/343
(58) Field of Search ................................. 250/345, 343, 250/575; 356/436, 437, 51

(56) References Cited

U.S. PATENT DOCUMENTS 5,331,409 A    7/1994  Thurtell et al.
6,040,915 A  * 3/2000  Wu et al. .................... 356/435

FOREIGN PATENT DOCUMENTS

| DE | 110 562 | 12/1974 |
|---|---|---|
| DE | 22 55 088 | 1/1975 |
| DE | 23 50 479 A1 | 4/1975 |
| DE | 27 49 229 | 2/1979 |
| DE | 31 07 617 A1 | 2/1982 |
| DE | 31 11 399 A1 | 10/1982 |
| DE | 427 037 | 10/1990 |
| DE | 058 182 | 3/1992 |
| DE | 197 35 599 A1 | 3/1999 |
| EP | 0 387 684 | 9/1990 |
| EP | 0 394 870 A1 | 10/1990 |
| GB | 2 228 568 A | 8/1990 |

* cited by examiner

*Primary Examiner*—Constantine Hannaher
*Assistant Examiner*—Timothy J. Moran
(74) *Attorney, Agent, or Firm*—Wall Marjama & Bilinski LLP

(57) ABSTRACT

The invention relates to an infrared gas analyser (1), especially for use as a gas detector for leak detection using a sampling probe. Said gas analyser comprises a vessel (test vessel 2), through which a test gas flows, and an infrared light source (4, 5, 42) which produces an infrared light that shines through the test vessel (2). The analyser further encompasses a detector (35) that facilitates measurement of the infrared light absorption in the test gas. The aim of the invention is to provide at low costs an analyser that is apt for every day use. To this end, a reference vessel (3) through which a reference gas flows is provided in addition to the test vessel (2) through which the test gas flows. A reference gas is sucked from the environment of the test gas suction area. The same or an additional light source (4, 5, 42) and the same detector (35) are allocated to said reference vessel. The analyser is provided with means (38, 41) that effect a modulation of the infrared light shining through the vessel (2, 3). Means (36) are provided which produce the measured values and which allow that the background signals obtained by the infrared absorption in the gas of the reference vessel (3) are taken into consideration for the signals obtained by measuring the infrared absorption in the test vessel.

19 Claims, 3 Drawing Sheets

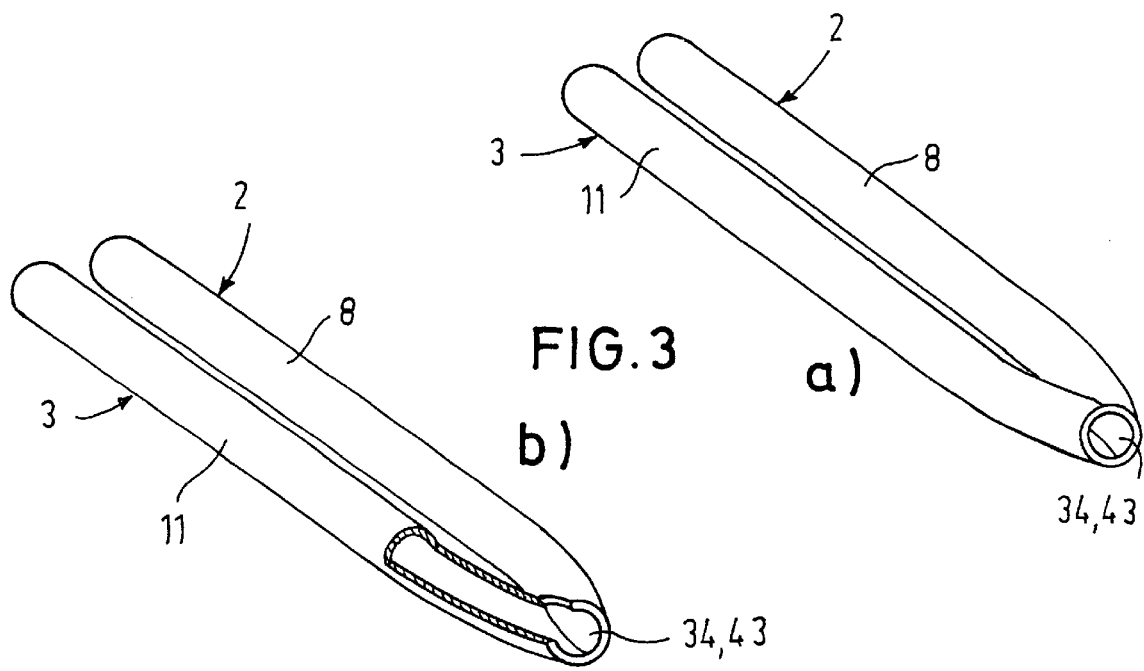
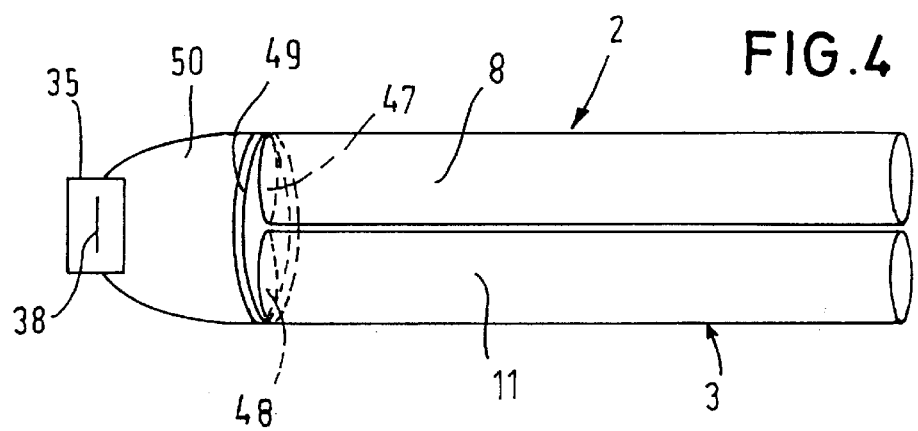

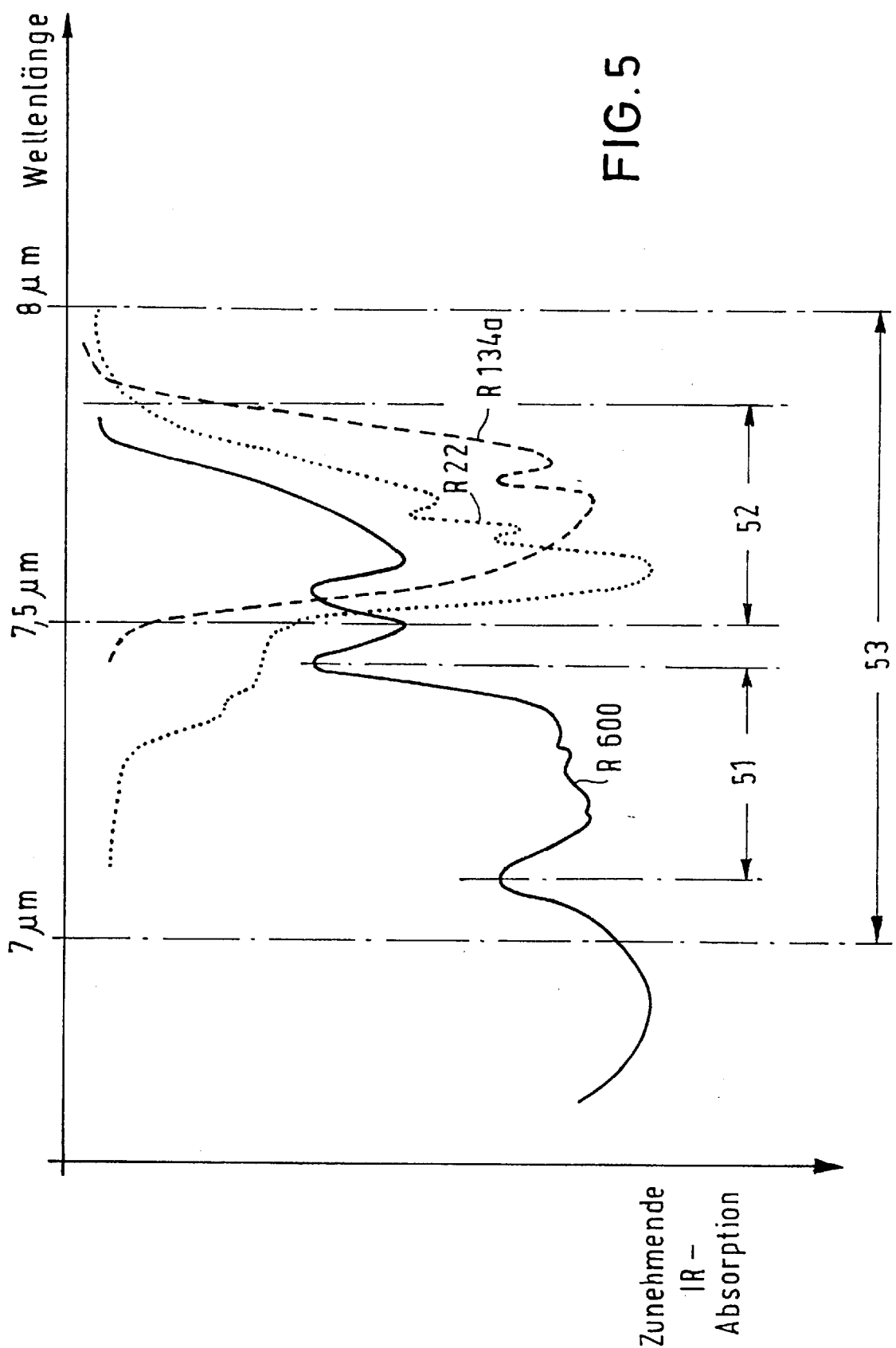

INFRARED GAS ANALYZER AND METHOD FOR OPERATING SAID ANALYZER

BACKGROUND OF THE INVENTION

The present invention relates to an infrared gas analyser, especially for deployment as a gas detector for leak detection based on the sampling probe principle, with a vessel (test vessel), through which the test gas flows, and an infrared light source which produces an infrared light that shines through the test vessel and with a detector that facilitates the measurement of the infrared light absorption in the test gas. Moreover, the present invention relates to a method for operating a gas analyser of this kind.

The principle of leak detection employing a sampling probe is frequently employed in the case of test samples which contain refrigerants or hydrocarbons (for example, condensers in refrigeration units). In this kind of leak detection, the media present in the test sample serve as the test or measurement gases. If a leak is present, small quantities of the test gas in each case will enter via the hose of the sampling probe into a gas detector which is so designed that it is capable of detecting these gases.

In relying on the sampling probe principle to detect leaks there exists the problem that at the probe tip not only test gases escaping from a possibly existing leak are taken in, but also gases may be taken in which are present in the environment of the probe's tip. If the latter already contain the test gas at a low concentration, for example, resulting from previously determined leaks or from the filling station of a production line, these will also be recorded by the gas detector. At high background levels for the test gas this may result in incorrect measurements, i.e. test samples which are leak tight are "detected" incorrectly as leaky.

Commonly, test gas detectors in leak detectors employ mass spectrometers. Mass spectrometers do offer a high detection sensitivity, but are costly and not particularly rugged.

The test gases mentioned above are active in the infrared range so that also an infrared gas analyser might be employed as the gas detector. The method of infrared absorption spectroscopy is basically known as a method of analysing gases (see, for example, Hansel/Neumann "Physik", Spektrum Akademie Verlag, Heidelberg). Spectrographs as detailed in this reference, however, are involved and sensitive instruments, not suited for everyday use in industry. Moreover, also known are industrial instruments (for example, MULTIWARN from the company Dräger) which, however, are by one or two orders of magnitude too insensitive for leak detection purposes and/or are, as to their response time, considerably too slow (30 to 60 seconds).

It is the task of the present invention to create an infrared gas analyser suitable for everyday work and which is cost-effective, which in particular may be employed as the gas detector in a leak detector. Moreover, by employing the infrared gas analyser, the aforementioned incorrect measurements to which the sampling probe principle is prone, shall be avoided.

SUMMARY OF THE INVENTION

This task is solved by the present invention for an infrared gas analyser of the aforementioned kind in that, besides the test vessel through which the test gas flows, there is present a reference vessel through which the reference gas flows which is taken in from the environment of the point at which the test gas is taken in, and where the same or a further source of light as well as the same detector is allocated to the reference vessel, that means are present effecting a modulation of the infrared light shining through the vessels, and that means for producing the measured values are present which allow the consideration of the background signals obtained by measuring the absorption of the infrared light in the gas of the reference vessel in the case of the signals which are obtained by measuring the infrared absorption in the test vessel. In that not only the test gas, but also the reference gas coming from the environment of the probe tip is analysed, all background concentrations in the test gas or of interfering other gases can be taken into account in the formation of the measured values. In the simplest case, the signals obtained by analysing the reference gas are subtracted from the signals obtained by analysing the test gas.

It is important that only a single infrared detector be employed, since the noise contributions from two different detectors are not correlated and will not vanish when subtracted. The use of a common source of infrared light or two separate light sources (one for each vessel) is possible. It is of significance that means be present which allow a modulation of the infrared light shining through the vessels, as otherwise the use of only a single detector would not be possible.

BRIEF DESCRIPTION OF THE DRAWINGS

Further advantages and details of the present invention shall be explained with reference to the implementation examples schematically depicted in drawing FIGS. 1 to 5. Depicted in drawing

DESCRIPTION OF THE INVENTION

Figure 1:
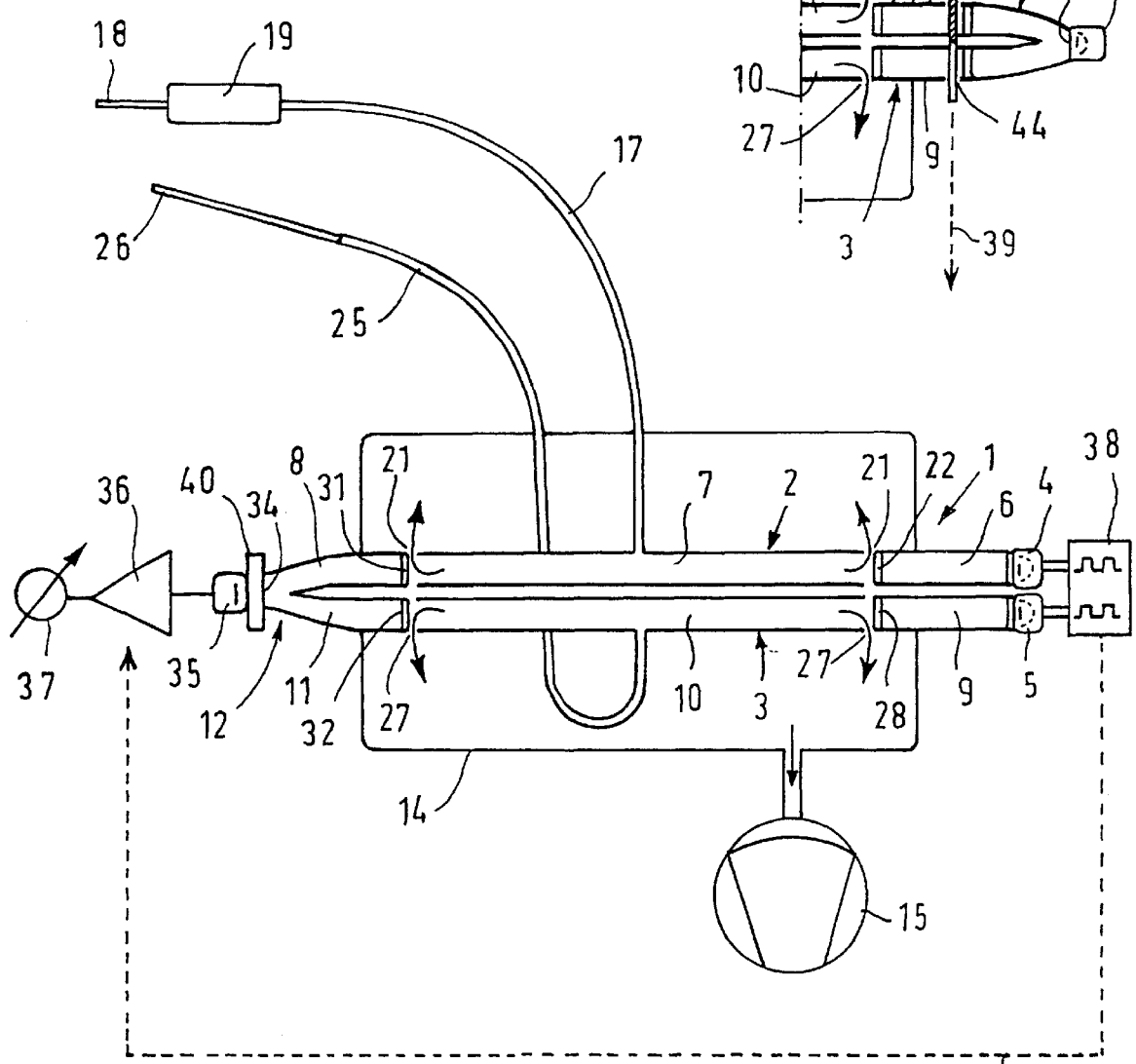
FIG. 1 is an implementation example for a gas analyser according to the present invention, drawing FIG. 2 an alternative for modulating the infrared light in accordance with drawing FIG. 1, drawing FIG. 3 an example of a dual beam tube, forming a test and reference vessel each, drawing FIG. 4 an alternative for focusing the light of both vessels on to a common detector and drawing FIG. 5 examples for gases active in the infrared range which are capable of being detected with the analyser according to the present invention.

The infrared gas analyser 1 according to drawing FIG. 1 comprises two vessels 2 and 3 to which each one infrared source of light 4 and 5 respectively is allocated. As a light source, infrared sources having a short thermal time constant are a possibility, which in particular may be designed as thin-film radiators. An example is model SVF350-5M3 from the company CAL-Sensors.

The vessels each consist of three sections 6, 7, 8 and 9, 10, 11 respectively. The middle sections 7, 10 of each are located within an enclosed chamber 14, to which the vacuum pump 15 (preferably a diaphragm pump) is connected.

In the design example presented, chamber 2 is the test chamber. The test gas flows through its middle section. To this end a test gas feed line (hose line 17) is connected at this section—for example at its middle, said feed line being linked to a sampling probe 18 with handpiece 19. For example, within the area of the two ends of section 7 there are located openings 21 (which, for example, may be designed as slots between the sections) which open out into the chamber 14, so that during operation the test gas is capable of flowing through section 7. The vacuum pump 15 serves the purpose of maintaining the flow of this gas. In addition, a feed pump might be arranged in handpiece 19.

Section 6 of the test vessel 2 is placed ahead of the infrared light source and extends into the chamber 14. The end of the test vessel facing section 7 is equipped with a gas-tight window 22 capable of passing infrared light. Thus maintaining of the pressure within the chamber 14 is ensured.

The reference vessel 3 is designed in a similar manner. It differs in that its middle section 10 is connected to a hose line 25, the intake opening 26 of which takes in gas from the environment of the sampling probe's tip 18. The openings of section 10 opening out into the chamber 14 are designated as 27, the window capable of passing infrared light of section 9 is designated as 28.

The sections 8 and 11 of the two vessels 2 and 3 are sealed off against the inside of the chamber 14 by windows 31, 32 capable of passing infrared light. Outside of chamber 14 they are designed in such a manner that they form a focusing facility 12, through which the light beams from the individual vessels 2, 3 are focused onto a detection surface. In the design example according to drawing FIG. 1 both vessels with their steadily approaching axes end in a joint opening 34. Located ahead of this opening 34 is an infrared detector 35, so that through this detector 35 infrared absorption measurements in both vessels 2 and 3 may be performed. The detector is preferably fitted in a light and gas-tight manner to the outlet opening of the joined vessels so that is mostly protected against interfering influences from its surroundings. As a cost-effective detector which is also usable in the medium infrared range, model LHi807TC from the company Heimann is suitable which is delivered with integrated temperature compensation. Connected to the detector 35 is an amplifier 36 and a measurement/display facility 37.

In order to be able to conduct the infrared absorption measurements in both vessels 2 and 3 one after the other, it is required to modulate the infrared light shining through the vessels. For this in the design example according to drawing FIG. 1 a frequency generator 38 is provided which is linked to the two sources of infrared light 4 and 5 modulating these. The frequency generator 38 generates periodic squarewave signals which are supplied to the light sources 4 and 5 shifted by 180 degrees. Moreover, the frequency generator 38 is linked via line 39 to the amplifier 36 so as to be able to apply the lock-in measurement technique. This measurement technique is basically known. It allows the detection of "noisy" signals at high sensitivity by modulating the wanted signal with subsequent phase-sensitive rectification.

Figure 2:
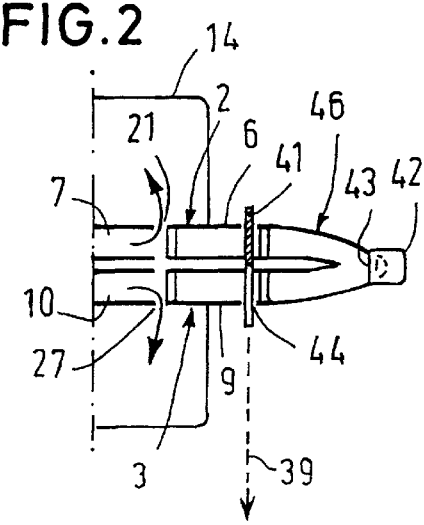

An other possibility of modulating the infrared light is the use of a mechanical chopper 41 (drawing FIG. 2). This solution offers the advantage of only one light source 42 being necessary. For this, the two sections 6 and 9 of the two vessels 2 and 3 are also designed in such a manner that these end in a joint opening 43 which is located ahead of the light source 42. Moreover, the sections 6 and 7 are interrupted outside of the chamber 14. In the thus created slot 44 there is located the chopper 41, which periodically controls in alternating fashion the passage of the infrared light through the vessels 2 and 3. With the chopper 41, also a reference signal may be generated which is supplied via the line 39 to the lock-in amplifier 36.

Depicted in drawing FIG. 3 is a design example for a dual beam tube, the structure of which allows it to be used as test and reference vessel 2 and 3 respectively. Its manufacture is effected in such a manner, that the ends of the individual tubes are initially bent and subsequently milled, such, that upon joining the ends of the individual tubes, a joint opening 34 and 43 respectively, is created. The two tubes preferably consist of pressed or extruded aluminium, the inside walls of which may additionally be coated with a well reflecting material.

In the implementation of the infrared gas analyser according to drawing FIG. 1, only one end of the dual tube is designed in the manner detailed. In the design example according to drawing FIG. 2, both end areas need to be designed in this manner. In the area of the joint infrared light source 42 (drawing FIG. 2) the split into two tubes as detailed has the effect of a beam splitter 46. Each of the partial beams reaches the detector 35 in the area where the tubes are joined again.

Instead of the focusing facility 12 detailed in connection with the design example according to drawing FIG. 1, also a paraboloidal-type reflector may be employed, the focus of which is located substantially at the plane of the detection surface. Depicted in drawing FIG. 4 is a design example of such a solution. Located ahead of the two outlet openings 47, 48 of the vessels which are sealed by a joint window 49 in a gas tight manner but with the capability of passing infrared light, is the paraboloidal-type reflector 50. Its focus is at the detection plane 38 of the detector 35. The paraboloidal-type reflector 50 is preferably a plastic part coated with a reflective coating of gold, silver or aluminium, and which on the one hand is adapted in its diameter to the outlets of the vessels 47, 48 and which on the other hand is adapted in its diameter to the detector. The detector 35 is, here too, fitted to the aperture of the paraboloidal-type reflector 50 in a light and gas-tight manner, which in turn through its window 49, allowing the passage of infrared light, is sealed off against the vacuum chamber 14 in a gas-tight manner.

With the application examples detailed for an infrared sensor designed according to the present invention, a detection sensitivity of under 1 ppm at a response time of about 1 second can be attained. Infrared sensors of this kind are rugged and thus usable in everyday industrial operation. The vessels can be manufactured without much complexity, so that they may be provided as a simple to exchange and cost-effective wearing component. This is of special significance in view of increasing contamination levels.

The analyser according to the present invention can be employed for gases active in the infrared range. In that a reference vessel is employed, there exists the possibility of subtracting from the total signal the background signal of the ambient atmosphere which may also contain other gases.

In order to obtain also a usable measurement signal (difference signal) when subtracting two large signals, an infrared filter is employed which allows that part of the spectrum to pass, in which the test gas exhibits a high absorption rate.

Since infrared filters of differing bandwidths are available there is the option, depending on the selected bandwidth, of varying the properties of the gas analyser. If, for example, a narrow-band filter is utilised, and provided a test gas has an absorption line within this range, then it is possible to detect precisely this gas only. If a very wide band filter is used, then practically any gas escaping from the leak can be detected, provided it has at least one absorption line within the very wide filter bandwidth. When choosing a suitable filter of medium bandwidth, some few test gases can be detected; specifically precisely those which have an absorption line within the selected filter bandwidth. The filter which defines the properties of the analyser is preferably fitted directly ahead of the detector 35. It is depicted schematically in drawing FIG. 1 and is designated as 40.

Depicted in drawing 5, for example, is the infrared absorption characteristic of three different refrigerants (R22, R134a, R600) in the wavelength range from 7 µm to 8 µm. The properties of infrared filters having different bandwidths are indicated by vertical dash-dot or dashed lines and double arrows.

For the sole detection of R600, for example, a relatively narrow-band infrared filter is employed, the properties of which are indicated by the double arrow 51. Only R600 has a high absorption rate within the bandwidth of this infrared filter.

A relatively narrow-band filter for the detection of preferably R22 or R134a is indicated by the double arrow 52. If equally R600 as well as R22 and R134a shall be detectable, a filter having a medium bandwidth, indicated by the double arrow 53, can be employed. However, in the case of an infrared detection of this kind, no statement can be gained as to which of the different gases is just being detected.

An example for an infrared filter which is usable for the gases depicted in drawing FIG. 5 is the filter FC-70520U of the company LOT Oriel, with a centre wavelength of 7.69 µm[1]) (for R134a) and a bandwidth of 4.2%.

[1]) Translator's note: The German text states "7,69 m" here whereas "7,69 µm" would be appropriate. Therefore "7,69 µm" has been assumed for the translation.

What is claimed is:

1. Infrared gas analyser (1), especially for use as a gas detector for leak detection using a sampling probe, with said gas analyser comprising a vessel (test vessel 2) through which a test gas flows, and an infrared light source (4, 5, 42) which produces an infrared light that shines through the test vessel (2) and a detector (35) that facilitates the measurement of the infrared light absorption in the test gas wherein a reference vessel (3) is provided in addition to the test vessel (2) through which the test gas flows, whereby a reference gas is sucked from the environment of the test gas suction area and flows through said reference vessel and where the same or an additional light source (4, 5, 42) and the same detector (35) are allocated to said reference vessel, where the analyser is provided with means (38, 41) that effect a modulation of the infrared light shining through the vessels (2, 3) and where means (36) are provided which produce the measured values and which allow that the background signals obtained by the infrared absorption in the gas of the reference vessel (3) are taken into consideration for the signals obtained by measuring the infrared absorption in the test vessel.

2. Analyser according to claim 1, wherein the test vessel (2) and the reference vessel (3) each comprise three sections (6, 7, 8 and 9, 10, 11 respectively) and where the test gas and the reference gas respectively flow through the middle section (7 and 10 respectively) of each.

3. Analyser according to claim 2, wherein lines (17, 25) are provided serving the purpose of supplying the test gas and the reference gas respectively, and where discharge openings (21 and 27) respectively open out within a vacuum chamber (14).

4. Analyser according to claim 3, wherein the light source(s) (4, 5 and 42 respectively) and the means (38, 41) for modulating the infrared light shining through the vessels (2, 3) are located within the sections (6–9) of the vessels.

5. Analyser according to claim 4, wherein to each of the sections (6, 9) of the vessels (2, 3) a light source (4 and 5 respectively) is allocated, and where for modulating the two infrared light sources (4, 5) a frequency generator (38) is provided.

6. Analyser according to claim 4, wherein only one light source (42) is provided the light of which is supplied to the vessels (2, 3) via a beam splitter (46), and where a mechanical chopper is provided for modulating the infrared light.

7. Analyser according to claim 3, wherein first inlet sections (6, 9) of said vessels protrude into the vacuum chamber (14) and are sealed rig inside by windows (22, 28) allowing infrared light to shine through.

8. Analyser according to claim 1, wherein second inlet sections (8, 11) of the vessels (2, 3) on the side of the detector also protrude into the vacuum chamber (14) and are sealed inside by windows (31, 32) allowing infrared light to shine through.

9. Analyser according to claim 8, wherein the sections (8, 11) of the vessels (2, 3) on the side of the detector which form the focusing facility (12) are designed in such a manner, that their axes steadily approach each other ending in a joint opening (34).

10. Analyser according to claim 1, wherein the infrared light shining through the vessels (2 and 3) is focused via a focusing facility (12) on to the detection surface.

11. Analyser according to claim 10, wherein a paraboloidal-type reflector is provided as the focusing facility (12).

12. Analyser according to claim 1, wherein a lock-in amplifier (36) is part of the means serving the purpose of forming the measured values.

13. Analyser according to claim 1, wherein the test and the reference chamber (2, 3) each consist of a metal tube—preferably of aluminum.

14. Analyser according to claim 13, wherein the two tubes, at least at their end sections, are designed in such a manner that their axes steadily approach each other ending in a joint opening (34, 43).

15. Analyser according to claim 13, wherein the inner walls of the tubes are coated with a reflecting metal.

16. Analyser according to one of the claims above, wherein there is located ahead of the detector (35) an infrared light filter (40).

17. Method for a operating a gas analyser as recited in claim 1, wherein infrared light absorption measurements are preformed in alternating fashion in the vessels (2, 3) and where the signals produced during the analysis of the reference gas in the reference vessel (3) are considered in the formation of the measured values.

18. Method according to claim 17, wherein the lock-in measurement technique is employed and where the necessary reference signals for this are generated by the modulating facility (38, 41 respectively).

19. Method according to claim 17, wherein the properties of the gas analyser are varied through the deployment of infrared filters (40) having different bandwidths.

* * * * *